(12) United States Patent
Hagberg et al.

(10) Patent No.: US 6,399,306 B1
(45) Date of Patent: Jun. 4, 2002

(54) GENETIC MARKERS WHICH IDENTIFY INDIVIDUALS WHO DECREASE THEIR BLOOD PRESSURE THROUGH EXERCISE

(75) Inventors: James M. Hagberg, Columbia, MD (US); Robert E. Ferrell, Pittsburgh, PA (US); Michael D. Brown, Laurel, MD (US)

(73) Assignee: University of Maryland, College Park Office of Technology Commercialization, College Park, MD (US)

( * ) Notice: Subject to any disclaimer, the term of this patent is extended or adjusted under 35 U.S.C. 154(b) by 0 days.

(21) Appl. No.: 09/622,910

(22) PCT Filed: Mar. 5, 1999

(86) PCT No.: PCT/JP99/03733

§ 371 (c)(1),
(2), (4) Date: Nov. 21, 2000

(87) PCT Pub. No.: WO99/45383

PCT Pub. Date: Sep. 10, 1999

Related U.S. Application Data

(60) Provisional application No. 60/077,226, filed on Mar. 7, 1998, provisional application No. 60/103,588, filed on Oct. 9, 1998, and provisional application No. 60/112,599, filed on Dec. 17, 1998.

(51) Int. Cl.[7] ................................................. C12Q 1/68
(52) U.S. Cl. .......................... 435/6; 436/63; 436/501; 436/503; 536/23.5; 536/27; 536/24.11; 935/11; 935/78; 935/77; 935/79; 435/91.1; 435/91.2
(58) Field of Search .......................... 435/6, 91.1, 91.2; 436/63, 501, 503; 536/23.5, 27, 24.31; 935/11, 78, 77, 79

(56) References Cited

U.S. PATENT DOCUMENTS 5,481,036 A    1/1996  Morishima et al.
6,156,510 A  * 12/2000  Griffiths et al. ................. 435/6

OTHER PUBLICATIONS

Hagberg et al., "Genetic Methods For Identifying Individuals For Improving Well Being And Performance Through Exercise", U.S. Application Ser. No. 09/620,579, filed Jul. 20, 2000.

Shuldiner, et al., "Genetic Markers Which Identify Individuals Who Improve Their Diabetes Status With Exercise", U.S. Applicaton Ser. No. 09/831,373, filed Aug. 21, 2001.

Williams, R.R., "Genetic Basis of Familial Dyslipidermia and Hypertension: 15–year Results from Utah", American Journal of Hypertension, Nov. 1993, vol. 6, No. 11, pp. 319S–327S.

Wu et al., "Quantitative Trait Locus Mapping of Human Blood Pressure to a G enetic Region at or Near the Lipoprotein Lipase G ene Locus on Chrom osome 8p22", Journal of Clinical Investigation, May 1996, vol. 97, No. 9, pp. 2111–2118.

Virolijk, L. et al., "Mutation Detection of Four Atherosclerosis High–Risk Genes and Correlations to Coronary Artery Disease", American Journal of Human Genetics, Oct. 1997, vol. 61, No. 4, Suppl. p. A225, Abstract No. 1306.

* cited by examiner

*Primary Examiner*—W. Gary Jones
*Assistant Examiner*—Janell E. Taylor
(74) *Attorney, Agent, or Firm*—Arent Fox Kintner Plotkin & Kahn

(57) ABSTRACT

Methods of reducing blood pressure levels in hypertensive subjects through the identification of subjects with an allele and/or genotype at a gene locus that positively correlates with improved success in reducing blood pressure levels, as compared to other alleles and/or genotypes at the same gene locus, and through the engagement of these subjects in exercise training for a period of time sufficient for the reduction of the subjects' blood pressure levels.

12 Claims, No Drawings

GENETIC MARKERS WHICH IDENTIFY INDIVIDUALS WHO DECREASE THEIR BLOOD PRESSURE THROUGH EXERCISE

This is a 371 of International Application Ser. No. PCT/US99/03733, filed on Mar. 5, 1999, which is based on U.S. Provisional Application No. 60/077,226, filed on Mar. 7, 1998, U.S. Provisional Application No. 60/103,588, filed on Oct. 9, 1998, and U.S. Provisional Application No. 60/112,599, filed Dec. 17, 1998.

FIELD OF THE INVENTION

The present invention relates to identifying one or more genetic markers which correlate with improved success in reducing blood pressure levels in hypertensive individuals.

BACKGROUND OF THE INVENTION

Studies have shown that individuals suffering from hypertension can alleviate symptoms or otherwise improve their conditions through exercise. Unfortunately, some individuals, no matter how rigorously they exercise, are unable to improve their conditions, while others benefit to a much greater extent than predicted. These results underscore the fact that many factors contribute to an individual's well-being. Such factors include, for example, behaviors such as diet and exercise, genetic makeup, and environment. While behavior and environment can be controlled, altered or regulated, an individual's genetic makeup is essentially predetermined and set at birth. The present inventors hypothesized that upon identifying the genetic makeup of a hypertensive population and observing that some individuals of the population lower their blood pressure from a change of behavior to a much greater or lesser extent than expected, a correlation could be made between the presence or absence of certain genetic markers and success in reducing blood pressure levels.

An object of the present invention is to identify one or more genetic markers which positively correlate with improved success in reducing blood pressure levels in hypertensive individuals.

SUMMARY OF THE INVENTION

The present inventors have discovered a number of genetic markers which positively correlate with improved success in reducing blood pressure levels in hypertensive individuals, as compared with other genetic makeup at the same gene loci. Therefore, the present invention is directed to a method of reducing blood pressure levels in a subject in need of such reduction, the method comprising:

identifying a subject having an allele and/or genotype at a particular gene locus which positively correlates with improved success in reducing blood pressure levels in hypertensive individuals, as compared with other alleles and/or genotypes at the same gene locus, wherein the subject is in need of reduced blood pressure levels, and engaging the subject in exercise training for a period of time sufficient to reduce blood pressure levels in the subject.

DETAILED DESCRIPTION OF THE INVENTION

The inventors have found that a number of genetic markers positively correlate with improved success in reducing blood pressure levels in hypertensive individuals, as compared with other genetic makeup at the same gene loci. Markers which the inventors have investigated include the lipoprotein lipase (LPL) gene PvuII and HindIII restriction sites, the angiotensin converting enzyme (ACE) gene insertion site, and the angiotensinogen M235T site.

The term "blood pressure" includes systolic blood pressure, diastolic blood pressure and mean blood pressure. A "reduction in blood pressure" may mean a reduction in systolic blood pressure and/or diastolic blood pressure and/or mean blood pressure. Such a reduction may include daytime blood pressure and/or nighttime blood pressure, or the reduction may be unrelated to time of day.

The term "single course of exercise", as used throughout this application, means a cardiovascular exercise session of any type which is conducted during one day. An exercise session may comprise an aerobics class, treadmill training, step machine, or any other suitable cardiovascular exercise regimen. For most cases, exercise may be completed in, for example, 30 minutes to 3 hours, with optional brief rest periods of 3–15 minutes, however this amount would vary depending on the health and endurance of the subject.

The term "extensive exercise" means about 10 single courses of exercise or more, preferably at least 15, at least 20, or at least 25 single courses of exercise, over a defined period of time ("the exercise period"). The exercise period in the case of an extensive exercise protocol may be from about 30–400 days, preferably from about 50–350 days or 70–300 days.

The term "limited exercise" means about 5 single courses of exercise or less, preferably at most 3, or 1 single course of exercise, over the exercise period. The exercise period in the case of a limited exercise protocol may be about 12 days or less, preferably at most 10, at most 7, or at most 5 days. It is most preferred that the limited exercise period be at most 3 days.

The term "moderate exercise" means about 5–9 single courses of exercise, preferably about 6–8, or 7 single courses of exercise, over the exercise period. The exercise period in the case of a limited exercise protocol may be from about 5–50 days, preferably from about 5–30 days, 5–20 days, or 5–15 days.

The time between exercise periods depends on whether the exercise period is an extensive, limited or moderate exercise period. In the case of extensive exercise periods, the time between exercise periods may be from about 10–120 days or more. In the case of limited exercise periods, the time between exercise periods may be from 4–60 days or more. In the case of moderate exercise periods, the time between exercise periods may be from 6–90 days or more. The term "between exercise periods" means that time during which the subject is not in an extensive, limited or moderate exercise program.

Lipoprotein lipase (LPL) is an enzyme that catalyzes the breakdown of triglycerides in the plasma to release free fatty acids. This hydrolysis also influences the metabolism of circulating lipoproteins. LPL has also been shown to enhance the triglyceride-rich chylomicron binding to low-density lipoprotein receptor-related proteins. Thus, LPL may also be an important regulator of chylomicron metabolism. The LPL gene is located on human chromosome 8p22. It is approximately 35 kilobases long and has 10 functionally differentiated exons. Two primary polymorphic variations occur at the LPL gene locus in frequencies that are important on a population basis. These two variations are detected by PvuII and HindIII restriction sites. There are three genotypes at each site, with the alleles for both PvuII and HindIII restriction sites denoted as "+" or "−", based on the presence or absence of a restriction site on that allele at the LPL locus with PvuII or HindIII. Thus, for both PvuII and HindIII there are three genotypes: +/+, +/− and −/−.

The present inventors have discovered that hypertensive individuals with different PvuII genotypes exhibit different degrees of success in reducing their blood pressure levels through exercise. These results could not have been predicted from initial patient screening.

The inventors have surprisingly discovered that each PvuII genotype potentially can benefit from exercise, however, the amount of exercise which produces the most benefits varies according to genotype. Specifically, the inventors have found that subjects having a "+/+" genotype for a PvuII restriction site exhibit more reduction in blood pressure levels than those with "+/−" or "−/−" genotypes, after extensive exercise. However, those subjects having "+/−" or "−/−" genotypes exhibit more reduction in blood pressure levels than those with "+/+" genotypes, after limited exercise.

Therefore, one method of reducing blood pressure levels in a subject in need of such reduction according to the invention comprises identifying a subject having a "+/+" genotype for a PvuII restriction site in a lipoprotein lipase gene, wherein the subject is in need of reduced blood pressure levels; and engaging the subject in extensive exercise training for a period of time sufficient to reduce the blood pressure levels in the subject.

Another method of reducing blood pressure levels in a subject in need of such reduction according to the invention comprises identifying a subject having at least one "−" allele or a "+/−" or "−/−" genotype for a PvuII restriction site in a lipoprotein lipase gene, wherein the subject is in need of reduced blood pressure levels; and engaging the subject in limited exercise training for a period of time sufficient to reduce the blood pressure levels in the subject.

The present inventors have also discovered that hypertensive individuals with different HindIII genotypes exhibit different degrees of success in reducing their blood pressure levels through exercise. These results could not have been predicted from initial patient screening.

The inventors have found that those individuals having "+/+" or "+/−" genotype for a HindIII restriction site exhibit more reduction in blood pressure levels than those with "−/−" genotypes, after extensive exercise. In addition, those subjects having "+/−" genotypes exhibit more reduction in blood pressure levels than those with "+/+" genotypes, after limited exercise.

Therefore, an additional method of reducing blood pressure levels in a subject in need of such reduction according to the invention comprises identifying a subject having at least one "+" allele or a "+/+" or "+/−" genotype for a HindIII restriction site in a lipoprotein lipase gene, wherein the subject is in need of reduced blood pressure levels; and engaging the subject in extensive exercise training for a period of time sufficient to reduce the blood pressure levels in the subject.

Another method of reducing blood pressure levels in a subject in need of such reduction according to the invention comprises identifying a subject having a "+/−" genotype for a HindIII restriction site in a lipoprotein lipase gene, wherein the subject is in need of reduced blood pressure levels; and engaging the subject in limited exercise training for a period of time sufficient to reduce the blood pressure levels in the subject.

Angiotensin converting enzyme (ACE) is the enzyme responsible for catalyzing the conversion of angiotensin I, a relatively inactive tissue and plasma vasopressor hormone, into the potent and highly active vasopressor hormone angiotensin II. This cascade of reactions is part of the renin-angiotensin-aldosterone system that has long been known to be an important regulator of arteriolar relaxation and vasoconstriction, and hence blood pressure, in humans and animals. The ACE gene is polymorphic with two common alleles designated "I" and "D", resulting in three genotypes: "I/I", "I/D" and "D/D". The "D" allele has a 287-base pair marker in intron 16 of the ACE gene deleted, whereas the "I" allele has the 287-base pair marker inserted. The "D" allele is associated with increased levels of ACE in both plasma and ventricular tissues. Increased levels of ACE will clearly contribute to increased myocardial and vascular smooth muscle growth and increased arteriolar vasoconstriction. Thus, the presence of the "D" allele is hypothesized to have deleterious effects on the cardiovascular system, and, in fact, the "D" allele has been associated with increased risk of left ventricular hypertrophy, cardiovascular disease, and sudden cardiovascular death.

The present inventors have discovered that hypertensive individuals with different ACE genotypes exhibit different degrees of success in reducing their blood pressure levels through exercise. These results could not have been predicted from initial patient screening.

The inventors have found that those individuals having "I/I" or "I/D" genotype for an ACE gene exhibit more reduction in blood pressure levels than those with "D/D" genotypes, after extensive exercise. However, those subjects having "I/I" or "D/D" genotypes exhibit more reduction in blood pressure levels than those with "I/D" genotypes, after limited exercise. In addition, those subjects having "I/I" genotypes exhibit more reduction in blood pressure levels than those with "I/D" or "D/D" genotypes, after moderate exercise.

Therefore, an additional method of reducing blood pressure levels in a subject in need of such reduction according to the invention comprises identifying a subject having at least one "I" allele or an "I/I" or "I/D" genotype for an ACE gene, wherein the subject is in need of reduced blood pressure levels; and engaging the subject in extensive exercise training for a period of time sufficient to reduce the blood pressure levels in the subject.

Another method of reducing blood pressure levels in a subject in need of such reduction according to the invention comprises identifying a subject having a "I/I" or "D/D" genotype for an ACE gene, wherein the subject is in need of reduced blood pressure levels; and engaging the subject in limited exercise training for a period of time sufficient to reduce the blood pressure levels in the subject.

Yet another method of reducing blood pressure levels in a subject in need of such reduction according to the invention comprises identifying a subject having a "I/I" genotype for an ACE gene, wherein the subject is in need of reduced blood pressure levels; and engaging the subject in moderate exercise training for a period of time sufficient to reduce the blood pressure levels in the subject.

Angiotensinogen (AGT) is the circulating protein substrate from which renin cleaves angiotensin I. AGT in the circulation originates in the liver. Human AGT is a glycoprotein with a molecular weight of approximately 57,000.

The method of the invention uses genetic variations at the M235T site (amino acid at position 235 changed from methionine (AUG) to threonine (ACG)) at the AGT gene locus to identify hypertensive persons who will reduce their blood pressure with exercise training. The inventors have found that hypertensives homozygous for either the "T" or the "M" allele decrease blood pressure more with extensive exercise training than those heterozygous at this loci. Hypertensives with the AGT "T/T" genotype decrease their systolic blood pressure more than those with the "M/M" or "M/T" genotype, while hypertensives with "M/M" genotype decrease their diastolic blood pressure more than those with the "T/T" or "M/T" genotype, with extensive exercise. In addition, those subjects having "T/T" genotype exhibit more reduction in blood pressure levels than those with "M/T" genotype, after limited exercise.

Therefore, a method of reducing blood pressure levels in a subject in need of such reduction according to the invention comprises identifying a subject having a "T/T" or "M/M" genotype for an AGT gene, wherein the subject is in need of reduced blood pressure levels; and engaging the subject in extensive exercise training for a period of time sufficient to reduce the blood pressure levels in the subject.

A method of reducing systolic blood pressure levels in a subject in need of such reduction according to the invention comprises identifying a subject having a "T/T" genotype for an AGT gene, wherein the subject is in need of reduced systolic blood pressure levels; and engaging the subject in extensive exercise training for a period of time sufficient to reduce the systolic blood pressure levels in the subject.

A method of reducing diastolic blood pressure levels in a subject in need of such reduction according to the invention comprises identifying a subject having a "M/M" genotype for an AGT gene, wherein the subject is in need of reduced diastolic blood pressure levels; and engaging the subject in extensive exercise training for a period of time sufficient to reduce the diastolic blood pressure levels in the subject.

Another method of reducing blood pressure levels in a subject in need of such reduction according to the invention comprises identifying a subject having a "T/T" genotype for an AGT gene, wherein the subject is in need of reduced blood pressure levels; and engaging the subject in limited exercise training for a period of time sufficient to reduce the blood pressure levels in the subject.

EXAMPLES

Example 1

Variations in Reduction of Blood Pressure in Subjects with Different LPLT PvuII and HindIII Genotypes After Extensive Exercise Obese sedentary hypertensive men ages 50–65 had DNA collected from them, and this DNA was analyzed for the presence of genetic variations at the LPL PvuII and HindIII restriction sites. DNA samples were subjected to amplification by the polymerase chain reaction in a Perkin-Elmer Cetus DNA Thermal Cycler. One set of primers was derived from sequences between exons 8 and 9 in the LPL gene to amplify the sequence around a HindIII restriction site in intron 8 (the forward primer was 5'-TTTAGGCCTGAAGTTTCCAC-3'[SEQ ID NO: 1], and the reverse primer was 5'-CTCCCTAGAAGAGAAGATC-3'[SEQ ID NO: 2]), as described in Kirchgessner et al., *PNAS* 86:9647–9651 (1989). The amplified fragment had a size of 1.3 kilobases.

The second set of primers was from the DNA sequences flanking the PvuII restriction site. In intron 6 (the forward primer was 5'-TAGGAGGTTGAGGCACCTGTGC-3'[SEQ ID NO: 3], and the reverse primer was 5'-GTGGGTGAATCACCTGAGGTC-3'[SEQ ID NO: 4]), as described in Oka et al., *Nucl. Acid Res.* 17:6752 (1989). This amplified fragment was 858 base pairs long.

The 50 $\mu$l reaction mixture contained 1×PCR buffer (10 mM Tris, pH 8.3, 50 mM KCl, 1.5 mM $MgCl_2$), dNTPs at 200 $\mu$M, 0.3 $\mu$M each primer, 0.5 $\mu$g genomic DNA, and 1.25 units of Taq DNA polymerase. Amplification of the region flanking the HindIII site was carried out for 33 cycles at 95° C. for 1 min, at 60° C. for 2 min, and at 72° C. for 2 min. For amplification around the PvuII site, the conditions were the same except for annealing at 70° C. and 25 cycles. Amplified products were digested with HindIII or PvuII and the resulting fragments were separated on 2% agarose gels. After digestion with HindIII, the presence of the restriction site ("+" allele) resulted in fragments of 600 and 700 base pairs. The presence of the PvuII restriction site ("+" allele) resulted in fragments of 266 and 592 base pairs.

The subjects participated in aerobic exercise training and were given the same diet. Specifically, to eliminate the effect of diet, all subjects were instructed in the principles of weight-maintaining American Heart Association (AHA) step I diet over an 8-week period before baseline testing. This diet consisted of 50–55% of calories as carbohydrate, 30–35% as fat, 15–20% as protein, 300–350 mg/day of cholesterol and 3 g/day of sodium. The subjects were counselled weekly to maintain their diet consumption throughout the length of monitoring. Adherence was monitored by registered dieticians who reviewed weekly food records and body weights and calculated dietary consumption from biweekly 7-day food records. At baseline and after the intervention, the subjects were weight-stable for 4 weeks before testing. During this period, the subjects were instructed to maintain their body weight within 1 kilogram.

The subjects took part in an aerobic exercise program that met 3 times per week for 9 months. Exercise training consisted of stationary cycling and walking and jogging on a treadmill starting at 51 60% of each individual's heart rate reserve for three five- to ten-minute periods. Target heart rate was calculated for each individual with the equation of Karvonen et al., *Ann. Med. Exp. Biol. Fenn.* 35:307–315 (1957).

Training intensity was gradually increased by five to ten percent of the heart rate reserve every month. At three months, the maximal oxygen consumption ($VO_{2max}$) test was repeated, and the intensity was adjusted until forty minutes of training per session at an intensity of seventy-five to eighty-five percent of heart rate reserve was achieved. All training sessions were supervised by the research staff, and the subjects were instructed by a dietician to increase the caloric intake to offset the increase in energy expenditure due to the increased physical activity.

Prior to having undergone exercise training and after undergoing the exercise regimen and associated diet, subjects were tested for systolic and diastolic blood pressure levels. Initial levels did not differ between hypertensive individuals with different LPL PvuII genotypes. However, the change in blood pressure resulting from exercise training did differ among LPL PvuII genotype groups (see Table 1). Those having only "+" alleles decreased both their systolic and diastolic blood pressures more with exercise training than those with "+/–" or "–/–" genotypes. In fact, both genotype groups decreased their systolic and diastolic blood pressure significantly with exercise training. However, those subjects with the "+/+" LPL PvuII genotype tended to decrease both their systolic and diastolic blood pressure more than those with the "+/–" or "–/–" genotypes.

TABLE 1

Changes in Blood Pressure with Exercise in LPL PvuII Genotype Groups

| Variable | "−/−" and "+/−" (n = 14) | "+/+" (n = 4) |
|---|---|---|
| Systolic Blood pressure (mmHg) | | |
| initial | 155 ± 10 | 156 ± 13 |
| change with training | −6 ± 8 | −14 ± 11 |
| Diastolic Blood pressure (mmHg) | | |
| initial | 95 ± 7 | 97 ± 8 |
| change with training | −5 ± 6 | −9 ± 9 |

These results indicate that LPL PvuII genotype is an indicator of those individuals most likely to reduce their systolic and diastolic blood pressure the most with exercise training.

In these same individuals, initial systolic blood pressure levels did not differ between hypertensive individuals with different LPL HindIII genotypes, but initial diastolic blood pressures were somewhat higher in the LPL HindIII "+/+" and "+/−" genotype group, compared to the "−/−" genotype group (94 vs. 86 mmHg). However, the changes in blood pressure resulting from exercise training did differ among LPL HindIII genotype groups (see Table 2). Those having at least one "+" allele decreased both their systolic and diastolic blood pressures significantly with exercise training. Furthermore, subjects with the "+/+" or "+/−" LPL HindIII genotype decreased both their systolic and diastolic blood pressures more than men with the "−/−" genotype.

TABLE 2

Changes in Blood Pressure with Exercise in LPL HindIII Genotype Groups

| Variable | "+/+" and "+/−" (n = 15) | "−/−" (n = 3) |
|---|---|---|
| Systolic Blood pressure (mmHg) | | |
| initial | 155 ± 11 | 149 ± 5 |
| change with training | −10 ± 8 | 3 ± 4 |
| Diastolic Blood pressure (mmHg) | | |
| initial | 94 ± 6 | 86 ± 6 |
| change with training | −9 ± 6 | 2 ± 3 |

These results indicate that LPL HindIII genotype is an indicator of those individuals most likely to reduce their systolic and diastolic blood pressure the most with exercise training.

Example 2

Variations in Reduction of Blood Pressure in Subjects with Different LPL PvuII and HindIII (Genotypes After One Single Course of Exercise A second group of older obese sedentary hypertensive men underwent two 24-hour ambulatory blood pressure recordings. One recording was on a day that was immediately preceded by 45 minutes of treadmill exercise at 75% of each subject's $VO_{2max}$. The second recording took place on another otherwise similar day without any prior exercise. The ambulatory blood pressure monitor was programmed to record blood pressures at a number of times per hour during each of the two 24-hour periods. LPL PvuII genotype groupings were conducted in a similar manner as in Example 1. The results are expressed as the difference in daytime, nighttime and 24-hour average blood pressures between the two days.

TABLE 3

Changes in Blood Pressure with Exercise in LPL PvuII Genotype Groups

| Variable | "−/−" and "+/−" (n= 6) | "+/+" (n = 2) | Probability |
|---|---|---|---|
| 24 hr systolic bp (mmHg) | | | |
| change with training | −10.7 ± 7.6 | −4.5 ± 2.1 | p = 0.19 |
| 24 hr diastolic bp (mmHg) | | | |
| change with training | −6.2 ± 4.1 | −3.0 ± 0 | p = 0.19 |
| 24 hr mean bp (mmHg) | | | |
| change with training | −7.5 ± 5.2 | −3.5 ± 0.7 | p = 0.19 |
| night systolic bp (mmHg) | | | |
| change with training | −9.3 ± 7.0 | −5.0 ± 2.8 | p = 0.25 |
| night diastolic bp (mmHg) | | | |
| change with training | −5.7 ± 2.9 | −1.5 ± 2.1 | p = 0.07 |
| night mean bp (mmHg) | | | |
| change with training | −7.2 ± 4.0 | −2.5 ± 2.1 | p = 0.10 |

Subjects with LPL PvuII "+/−" or "−/−" genotypes decreased blood pressure more than otherwise similar subjects having "+/+" genotypes after one single course of exercise.

In these same individuals, LPL HindIII "+/+" and "+/−" genotypes were examined to determine whether genotype indicates subjects who will benefit more from one single course of exercise. The results are found in Table 4.

TABLE 4

Changes in Blood Pressure with Exercise in LPL HindIII Genotype Groups

| Variable | "+/−" (n = 2) | "+/+" (n = 6) | Probability |
|---|---|---|---|
| night systolic bp (mmHg) | | | |
| change with training | −15.5 ± 7.8 | −5.8 ± 4.0 | p = 0.04 |
| night diastolic bp (mmHg) | | | |
| change with training | −8.0 ± 2.8 | −3.5 ± 2.6 | p = 0.06 |
| night mean bp (mmHg) | | | |
| change with training | −10.5 ± 3.5 | −4.5 ± 3.2 | p = 0.04 |

Subjects with LPL HindIII "+/−" genotypes decreased blood pressure more than otherwise similar subjects having "+/+" genotypes after one single course of exercise.

Example 3

Variations in Reduction of Blood Pressure in Subjects with Different ACE Genotypes After Extensive Exercise The subjects described in Example 1 had their DNA analyzed for the identities of their ACE alleles. Typing of these individuals was conducted by isolating high molecular weight genomic DNA from whole blood mononuclear cells by the procedure of Miller et al. *Nucl. Acids Res.* 16:1215–1218 (1988). ACE genotyping was carried out by the polymerase chain reaction amplification using the forward primer 5'-CCGTTTGTGCAGGGCCTGGCTCTCT-3' [SEQ ID NO: 5] and reverse primer 5'-CAGGGTGCTGTCCACACTGGACCCC-3'[SEQ ID NO: 6] and the following cyclic conditions: denaturation at 95° C. for 5 min, followed by 30 cycles of 30 sec denaturation at 94° C., 15 sec annealing at 58° C., 30 sec extension at 72° C. Amplimers were resolved on 2% agarose gels and genotypes were assigned by direct comparisons to samples of known genotype. The "I" allele yielded a band of 490 base pairs and the "D" allele yielded a band of 190 base pairs. Heterozygotes were typed by the presence of both bands plus a heteroduplex band migrating at approximately 370 base pairs (Tiret et al. *Am. J. Hum. Genet.* 51:197–205 (1992).

The subjects were challenged with aerobic exercise training (3 times per week for 9 months) and were given the same diet, as described in Example 1. All subjects were instructed in the principles of weight-maintaining American Heart Association step I diet over an 8-week period before baseline testing, as reported in Example 1. The subjects were counselled weekly to maintain their diet, as reported in Example 1. Adherence was monitored, as reported in Example 1.

Subjects had their blood pressure measured weekly for 4 weeks prior to and following the completion of the exercise training intervention. The final values at baseline and after the intervention represent the average of 12 independent blood pressure measurements (3 on each of the 4 measurement days).

Results of this study indicate that ACE genotype identifies hypertensive individuals that reduce their systolic and diastolic blood pressure with exercise training. Those subjects with at least one insertion "I" allele decreased their diastolic blood pressure with extensive exercise training approximately 7 times more than those with only "D" alleles. Subjects with at least one "I" allele decreased their systolic blood pressure with exercise training over twice as much as those with only "D" alleles.

TABLE 5

Changes in Blood Pressure with Exercise in ACE Genotype Groups

| Variable | "I/I" and "I/D" (n = 11) | "D/D" (n = 8) | Probability |
|---|---|---|---|
| Systolic bp (mmHg) | | | |
| change with training | −9.8 ± 9.6 | −4.7 ± 8.0 | p = 0.14 |
| Diastolic bp (mmHg) | | | |
| change with training | −10.0 ± 6.0 | −1.4 ± 5.0 | p < 0.005 |

These results show that ACE genotype is a strong independent indicator of those individuals who will reduce their systolic and diastolic blood pressure with extensive exercise training.

Example 4

Variations in Reduction of Blood Pressure in Subjects with Different ACE Genotypes After One Single Course of Exercise The subjects described in Example 2 underwent two 24-hour ambulatory blood pressure recordings, as reported in Example 2. One recording was on a day that was immediately preceded by 45 minutes of treadmill exercise at 75% of each subject's $VO_{2max}$. The second recording took place on another otherwise similar day without any prior exercise. The ambulatory blood pressure monitor was programmed to record blood pressures at a number of times per hour during each of the two 24-hour periods. ACE genotype grouping was conducted in a manner similar to Example 3. The results are expressed as the difference in daytime and 24-hour average blood pressures between the two days.

TABLE 6

Changes in Blood Pressure with Exercise in ACE Genotype Groups

| Variable | "I/I" and "D/D" (n = 6) | "I/D" (n = 6) | Probability |
|---|---|---|---|
| 24 hr diastolic bp (mmHg) | | | |
| change with training | −6.2 ± 3.3 | −3.0 ± 5.7 | p = 0.20 |
| day diastolic bp (mmHg) | | | |
| change with training | −7.8 ± 4.3 | 0 ± 5.7 | p = 0.07 |
| day mean bp (mmHg) | | | |
| change with training | −9.7 ± 6.2 | −3.0 ± 8.5 | p = 0.19 |

These results show that ACE genotype is a strong independent indicator of those individuals who will reduce their blood pressure with single courses of exercise training.

Example 5

Variations in Reduction of Blood Pressure in Subjects with Different ACE Genotypes After Moderate Exercise A group of obese sedentary hypertensive women (ages 40–63) underwent 7 days of exercise training to quantify their reductions in ambulatory blood pressure. Subjects were initially weight-stabilized on their own diet and then underwent a 24-hour recording of their blood pressure while they underwent their usual daily activities. The women then repeated the blood pressure recording after 7 days of exercise training. The training consisted of 7 consecutive days of treadmill walking and cycle ergometry. The subjects walked on a treadmill for 30 minutes, followed by 5 minutes of rest, and then 20 additional minutes of treadmill walking or cycle ergometry.

The blood pressure values from the two recordings were averaged over the entire 24-hour period, and over the day and night portions of the recordings. ACE genotye grouping was conducted in a manner similar to Example 3. The results are reported in the following Table.

TABLE 7

Changes in Blood Pressure with Exercise in ACE Genotype Groups

| Variable | "I/I" (n = 4) | "I/D" and "D/D" (n = 2) | Probability |
|---|---|---|---|
| 24 hr diastolic bp (mmHg) | | | |
| change with training | −4.5 ± 4.9 | −0.3 ± 22.1 | p = 0.18 |
| 24 hr mean bp (mmHg) | | | |
| change with training | −4.5 ± 2.1 | 0 ± 2.2 | p = 0.07 |
| day systolic bp (mmHg) | | | |
| change with training | −5.0 ± 0 | −1.0 ± 2.9 | p = 0.14 |
| night systolic bp (mmHg) | | | |

TABLE 7-continued

Changes in Blood Pressure with Exercise in ACE Genotype Groups

| Variable | "I/I" (n = 4) | "I/D" and "D/D" (n = 2) | Probability |
|---|---|---|---|
| change with training night diastolic bp (mmHg) | −9.0 ± 2.8 | 0.8 ± 4.6 | p = 0.06 |
| change with training night mean bp (mmHg) | −12.0 ± 1.4 | −0.5 ± 4.5 | p = 0.03 |
| change with training | −6.5 ± 4.9 | 0 ± 4.1 | p = 0.16 |

The results show that ACE genotype is an indicator of those individuals who will reduce their blood pressure with moderate exercise training.

Example 6

Variations in Reduction of Blood Pressure in Subjects with Different AGT Genotypes After Extensive Exercise The subjects described in Example I had their DNA analyzed for the identities of their AGT alleles. The A(−20)C promoter polymorphism was genotyped by PCR amplification using unique sequence flanking primers, as described in Ishigami et al. *Hypertension* 30:1325–1330, followed by detection using an allele specific oligonucleotide ligation assay, as described in Nickerson et al. *Proc. Natl. Acad. Sci. USA* 87:2923–2927 (1990). The M235T polymorphism was typed by amplification using the exon 2 primers described in Jeunemaitre et al. *Cell* 71:169–180 (1992), followed by detection using an oligonucleotide ligation assay (as described in Nickerson et al., supra).

The subjects were challenged with aerobic exercise training (3 times per week for 9 months) and were given the same diet, as described in Example 1. All subjects were instructed in the principles of weight-maintaining American Heart Association step I diet over an 8-week period before baseline testing, as reported in Example 1. The subjects were counselled weekly to maintain their diet, as reported in Example 1. Adherence was monitored, as reported in Example 1.

Subjects had their blood pressure measured weekly for 4 weeks prior to and following the completion of the exercise training intervention. The final values at baseline and after the intervention represent the average of 12 independent blood pressure measurements (3 on each of the 4 measurement days).

Results of this study indicate that AGT genotype identifies hypertensive individuals that reduce their systolic and diastolic blood pressure with exercise training. Those subjects with a "M/M" or "T/T" genotype decreased their systolic and diastolic blood pressure with extensive exercise training more than those with heterozygous genotype. Results are presented in Table 8.

TABLE 8

Changes in Blood Pressure with Exercise in AGT Genotype Groups

| Variable | "T/T" (n = 5) | "M/T" (n = 9) | "M/M" (n = 2) |
|---|---|---|---|
| Systolic bp (mmHg) | | | |
| change with training Diastolic bp (mmHg) | −12 ± 4 | −5 ± 2 | −11 ± 17 |
| change with training | −7 ± 2 | −6 ± 2 | −9 ± 13 |

These results show that AGT genotype is an indicator of those individuals who will reduce their systolic and diastolic blood pressure with extensive exercise training.

Example 7

Variations in Reduction of Blood Pressure in Subjects with Different AGT Genotypes After One Single Course of Exercise The group of older obese sedentary hypertensive men described in Example 2 underwent two 24-hour ambulatory blood pressure recordings, as described in Example 2, one recording on a day preceded by exercise and the second recording on another otherwise similar day without any prior exercise. Blood pressure was recorded as described in Example 2. AGT genotype groupings were conducted in a similar manner as in Example 6. The results are expressed as the difference in daytime, nighttime and 24-hour average blood pressures between the two days.

TABLE 9

Changes in Blood Pressure with Exercise in AGT Genotype Groups

| Variable | "T/T" (n = 3) | "M/T" (n = 2) |
|---|---|---|
| 24 hr systolic bp (mmHg) | | |
| change with training 24 hr diastolic bp (mmHg) | −16.3 ± 3.2 | −5.3 ± 1.8 |
| change with training 24 hr mean bp (mmHg) | −9.0 ± 1.1 | −3.3 ± 1.5 |
| change with training day systolic bp (mmHg) | −11.3 ± 1.4 | −3.8 ± 1.7 |
| change with training day diastolic bp (mmHg) | −19.3 ± 4.7 | −6.0 ± 3.7 |
| change with training day mean bp (mmHg) | −9.7 ± 3.2 | −3.8 ± 2.7 |
| change with training night systolic bp (mmHg) | −13.7 ± 3.7 | −4.5 ± 2.8 |
| change with training night diastolic bp (mmHg) | −13.3 ± 4.3 | −4.8 ± 1.8 |
| change with training night mean bp (mmHg) | −7.7 ± 1.2 | −2.8 ± 1.3 |
| change with training | −9.7 ± 2.0 | −3.8 ± 1.6 |

The results show that AGT genotype clearly identifies those subjects who decrease their blood pressure more than other individuals.

We claim:

1. A method of reducing blood pressure levels in a hypertensive subject, the method comprising:

identifying a hypertensive subject having an allele and/or genotype at the LPL gene PvuII and HindIII restriction sites, the ACE gene insertion site, and/or the angiotensinogen M235T site which positively correlate to a higher reduction of blood pressure levels as a result of exercise, as compared with other alleles and/or genotypes at the same gene locus; and engaging the subject in exercise training for a period of time sufficient to reduce blood pressure levels in the subject.

2. A method of reducing blood pressure levels in a subject in need of such reduction, the method comprising:

identifying a subject having a "+/+" genotype for a PvuII restriction site in a lipoprotein lipase gene, wherein the subject is in need of reduced blood pressure levels; and engaging the subject in extensive exercise training for a period of time sufficient to reduce the blood pressure levels in the subject.

3. A method of reducing blood pressure levels in a subject in need of such reduction, the method comprising:

identifying a subject having at least one "−" allele or a "+/−" or "−/−" genotype for a PvuII restriction site in a lipoprotein lipase gene, wherein the subject is in need of reduced blood pressure levels; and engaging the subject in limited exercise training for a period of time sufficient to reduce the blood pressure levels in the subject.

4. A method of reducing blood pressure levels in a subject in need of such reduction, the method comprising:

identifying a subject having at least one "+" allele or a "+/+" or "+/−" genotype for a HindIII restriction site in a lipoprotein lipase gene, wherein the subject is in need of reduced blood pressure levels; and engaging the subject in extensive exercise training for a period of time sufficient to reduce the blood pressure levels in the subject.

5. A method of reducing blood pressure levels in a subject in need of such reduction, the method comprising:

identifying a subject having a "+/−" genotype for a HindIII restriction site in a lipoprotein lipase gene, wherein the subject is in need of reduced blood pressure levels; and engaging the subject in limited exercise training for a period of time sufficient to reduce the blood pressure levels in the subject.

6. A method of reducing blood pressure levels in a subject in need of such reduction, the method comprising:

identifying a subject having at least one "I" allele or an "I/I" or "I/D" genotype for an angiotensin converting enzyme gene, wherein the subject is in need of reduced blood pressure levels; and engaging the subject in extensive exercise training for a period of time sufficient to reduce the blood pressure levels in the subject.

7. A method of reducing blood pressure levels in a subject in need of such reduction, the method comprising:

identifying a subject having a "I/I" or "D/D" genotype for an angiotensin converting enzyme gene, wherein the subject is in need of reduced blood pressure levels; and engaging the subject in limited exercise training for a period of time sufficient to reduce the blood pressure levels in the subject.

8. A method of reducing blood pressure levels in a subject in need of such reduction, the method comprising:

identifying a subject having a "I/I" genotype for an angiotensin converting enzyme gene, wherein the subject is in need of reduced blood pressure levels; and engaging the subject in moderate exercise training for a period of time sufficient to reduce the blood pressure levels in the subject.

9. A method of reducing blood pressure levels in a subject in need of such reduction, the method comprising:

identifying a subject having a "T/T" or "M/M" genotype for an angiotensinogen gene, wherein the subject is in need of reduced blood pressure levels; and engaging the subject in extensive exercise training for a period of time sufficient to reduce the blood pressure levels in the subject.

10. A method of reducing systolic blood pressure levels in a subject in need of such reduction, the method comprising:

identifying a subject having a "T/T" genotype for an angiotensinogen gene, wherein the subject is in need of reduced systolic blood pressure levels; and engaging the subject in extensive exercise training for a period of time sufficient to reduce the systolic blood pressure levels in the subject.

11. A method of reducing diastolic blood pressure levels in a subject in need of such reduction, the method comprising:

identifying a subject having a "M/M" genotype for an angiotensinogen gene, wherein the subject is in need of reduced diastolic blood pressure levels; and engaging the subject in extensive exercise training for a period of time sufficient to reduce the diastolic blood pressure levels in the subject.

12. A method of reducing blood pressure levels in a subject in need of such reduction, the method comprising:

identifying a subject having a "T/T" genotype for an angiotensinogen gene, wherein the subject is in need of reduced blood pressure levels; and engaging the subject in limited exercise training for a period of time sufficient to reduce the blood pressure levels in the subject.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Homo sapiens

<400> SEQUENCE: 1
tttaggcctg aagtttccac                    20

<210> SEQ ID NO 2
<211> LENGTH: 19
<212> TYPE: DNA
<213> ORGANISM: Homo sapiens

<400> SEQUENCE: 2
ctccctagaa gagaagatc                     19

<210> SEQ ID NO 3
<211> LENGTH: 22
<212> TYPE: DNA
<213> ORGANISM: Homo sapiens

<400> SEQUENCE: 3
taggaggttg aggcacctgt gc                 22

<210> SEQ ID NO 4
<211> LENGTH: 21
<212> TYPE: DNA
<213> ORGANISM: Homo sapiens

<400> SEQUENCE: 4
gtgggtgaat cacctgaggt c                  21

<210> SEQ ID NO 5
<211> LENGTH: 25
<212> TYPE: DNA
<213> ORGANISM: Homo sapiens

<400> SEQUENCE: 5
ccgtttgtgc agggcctggc tctct              25

<210> SEQ ID NO 6
<211> LENGTH: 25
<212> TYPE: DNA
<213> ORGANISM: Homo sapiens

<400> SEQUENCE: 6
cagggtgctg tccacactgg acccc              25